(12) United States Patent
Denham

(10) Patent No.: US 10,548,586 B2
(45) Date of Patent: Feb. 4, 2020

(54) FIXATION DEVICES METHODS AND SYSTEMS FOR SOFT TISSUE REPAIR

(71) Applicant: Zimmer, Inc., Warsaw, IN (US)

(72) Inventor: Gregory J. Denham, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 388 days.

(21) Appl. No.: 15/338,945

(22) Filed: Oct. 31, 2016

(65) Prior Publication Data

US 2017/0119367 A1 May 4, 2017

Related U.S. Application Data

(60) Provisional application No. 62/250,719, filed on Nov. 4, 2015.

(51) Int. Cl.
*A61B 17/04* (2006.01)

(52) U.S. Cl.
CPC ...... *A61B 17/0401* (2013.01); *A61B 17/0467* (2013.01); *A61B 17/0485* (2013.01); *A61B 2017/0403* (2013.01); *A61B 2017/045* (2013.01); *A61B 2017/0409* (2013.01); *A61B 2017/0412* (2013.01); *A61B 2017/0414* (2013.01)

(58) Field of Classification Search
CPC ............ A61B 17/0401; A61B 17/0467; A61B 17/0485; A61B 2017/0403; A61B 2017/0409; A61B 2017/0412; A61B 2017/0414; A61B 2017/045; A61B 2017/0441; A61B 2017/0437; A61B 2017/0435; A61B 2017/042; A61B 2017/043; A61B 2017/044; A61B 2017/0446

See application file for complete search history.

(56) References Cited

U.S. PATENT DOCUMENTS 5,849,004 A 12/1998 Bramlet
6,146,407 A 11/2000 Krebs
(Continued)

OTHER PUBLICATIONS

"CinchLock Knotless Anatomic Labrum Restoration System", [Online]. Retrieved from the Internet: <URL: http://www.mckenzieillustrations.com/downloads/lit02289a_cinchlock%20surgical%20technique.pdf, 6 pgs.
(Continued)

*Primary Examiner* — Erich G Herbermann
(74) *Attorney, Agent, or Firm* — Schwegman Lundberg & Woessner, P.A.

(57) ABSTRACT

Methods, systems and apparatuses for soft tissue repair including a device for anchoring sutured tissue to bone are disclosed. In one example, a device can include a body and a member. The body can have a wall with an outer surface thereof configured to engage the bone of a patient. The body can define an inner passage extending generally from a proximal end thereof to a distal end thereof. The body can have a slit formed by the wall, the slit extending at least a portion of a proximal-distal length of the wall. The member can be configured to be disposed within the body and can be moveable along the inner passage relative to the body between a first position and a second position. The member can be configured with a second passage to receive and pass a suture through the member when the member is in the first position.

26 Claims, 12 Drawing Sheets

(56) References Cited

U.S. PATENT DOCUMENTS

| | | |
|---|---|---|
| 7,976,565 B1* | 7/2011 | Meridew .............. A61B 17/0401 606/232 |
| 8,221,433 B2 | 7/2012 | Lozier |
| 10,327,754 B2 | 6/2019 | Denham |
| 2011/0264140 A1* | 10/2011 | Lizardi .............. A61B 17/0401 606/232 |
| 2012/0078298 A1 | 3/2012 | Sklar |
| 2013/0096611 A1* | 4/2013 | Sullivan ............. A61B 17/0485 606/232 |
| 2013/0267998 A1 | 10/2013 | Vijay et al. |
| 2016/0310128 A1 | 10/2016 | Denham |

OTHER PUBLICATIONS

"Dr. Charles Nofsinger—Hitch Stitch Using 2.8mm PopLok® Suture Anchor—ConMed", youtube, [Online]. Retrieved from the Internet: https://www.youtube.com/watch?v=4sTR1HCr9Fw, (Jan. 21, 2013), 1 pg.

"Linvatec Shoulder Restoration System", [Online]. Retrieved from the Internet: <URL: http://www.endoprotez.com/pdf/CBR3045_PopLok.pdf, (2009), 2 pgs.

"U.S. Appl. No. 15/134,002, Notice of Allowance dated Feb. 14, 2019", 13 pgs.

"U.S. Appl. No. 15/134,002, Response filed Jun. 4, 2018 to Restriction Requirmeent dated Mar. 5, 2018", 7 pgs.

"U.S. Appl. No. 15/134,002, Non Final Office Action dated Jul. 26, 2018", 15 pgs.

U.S. Appl. No. 15/134,002, Response filed Oct. 26, 2018 to Non Final Office Action dated Jul. 26, 2018, 16 pgs.

"U.S. Appl. No. 15/134,002, Corrected Notice of Allowability dated Apr. 10, 2019", 7 pgs.

* cited by examiner

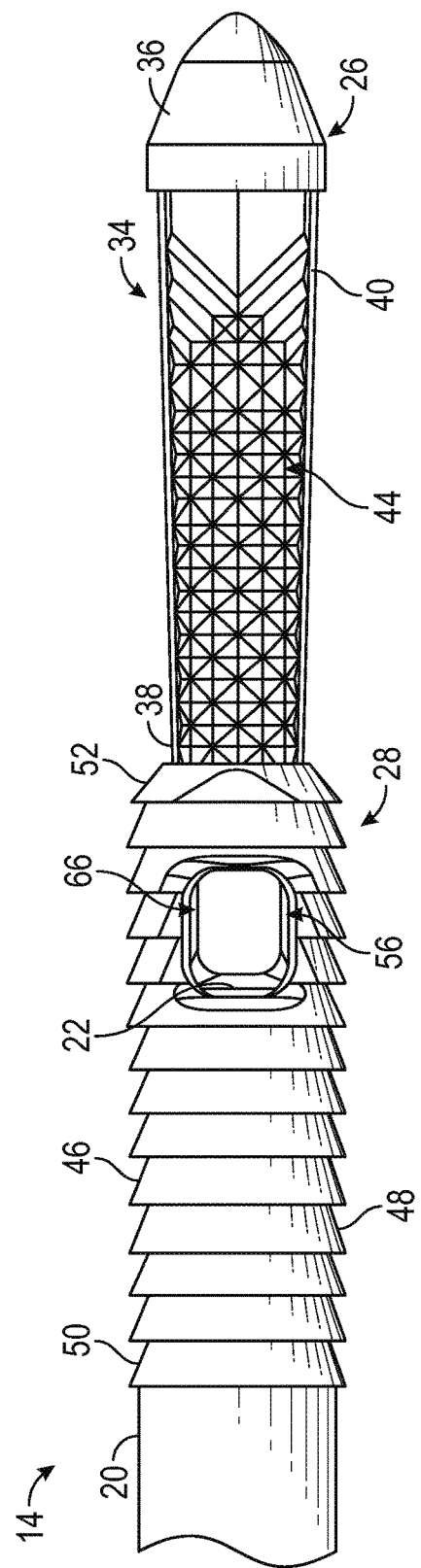

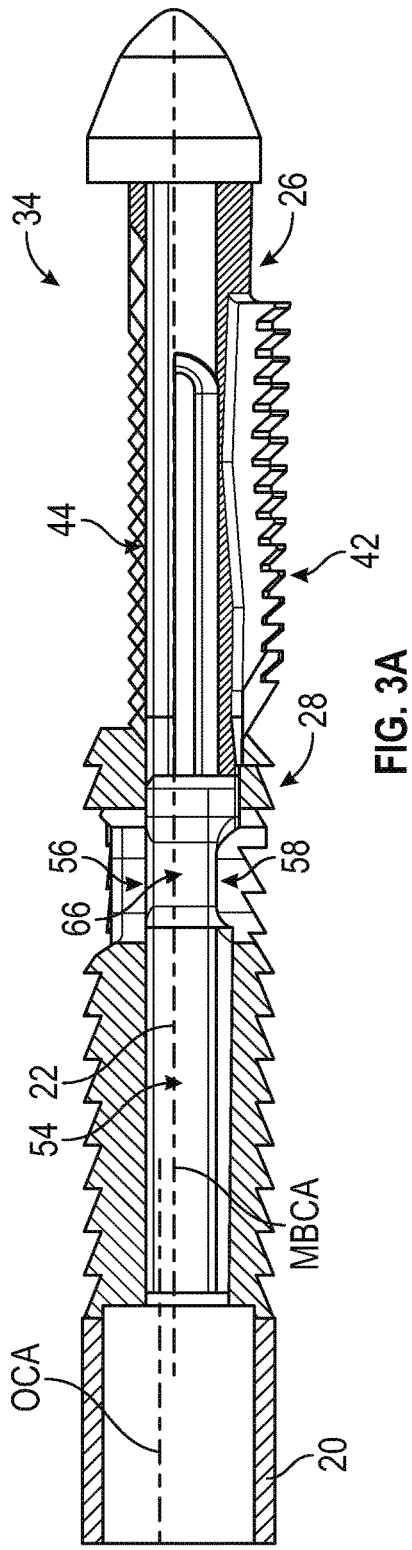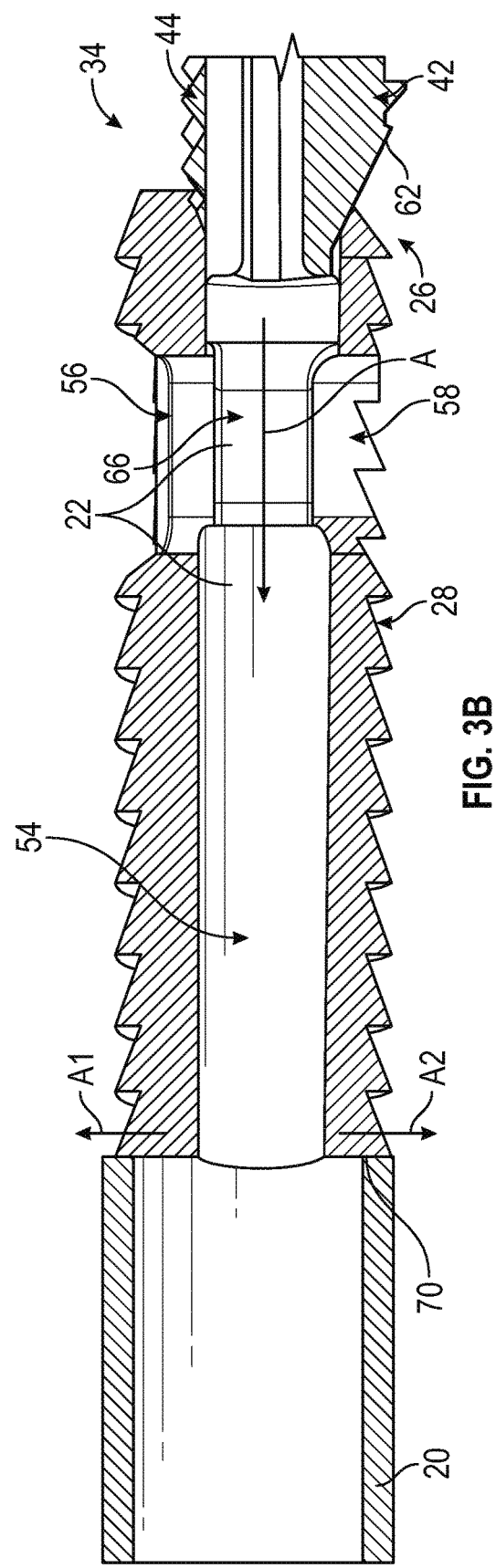
FIG. 3A
FIG. 3B

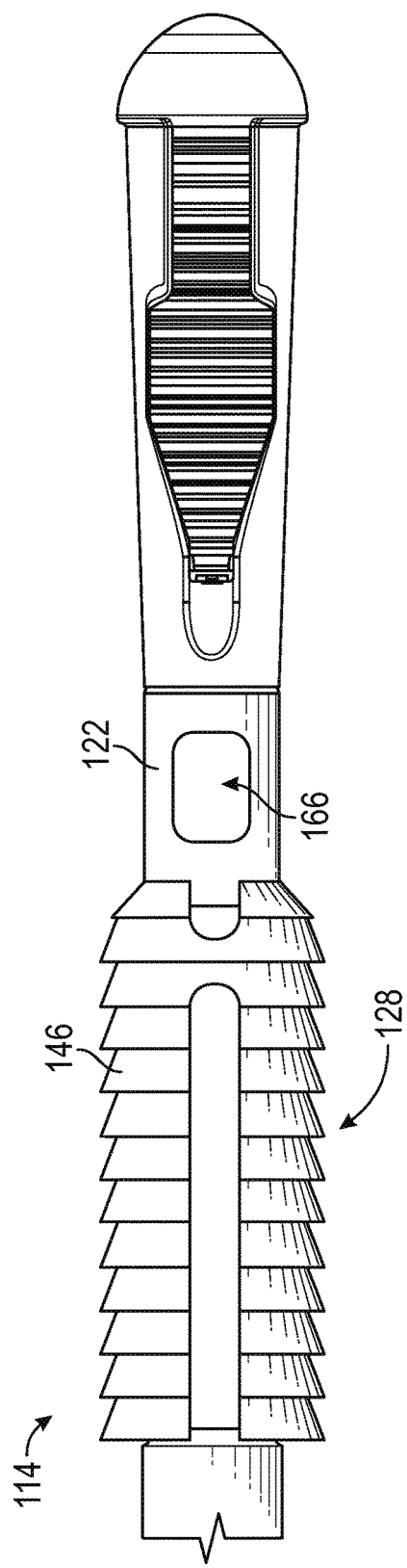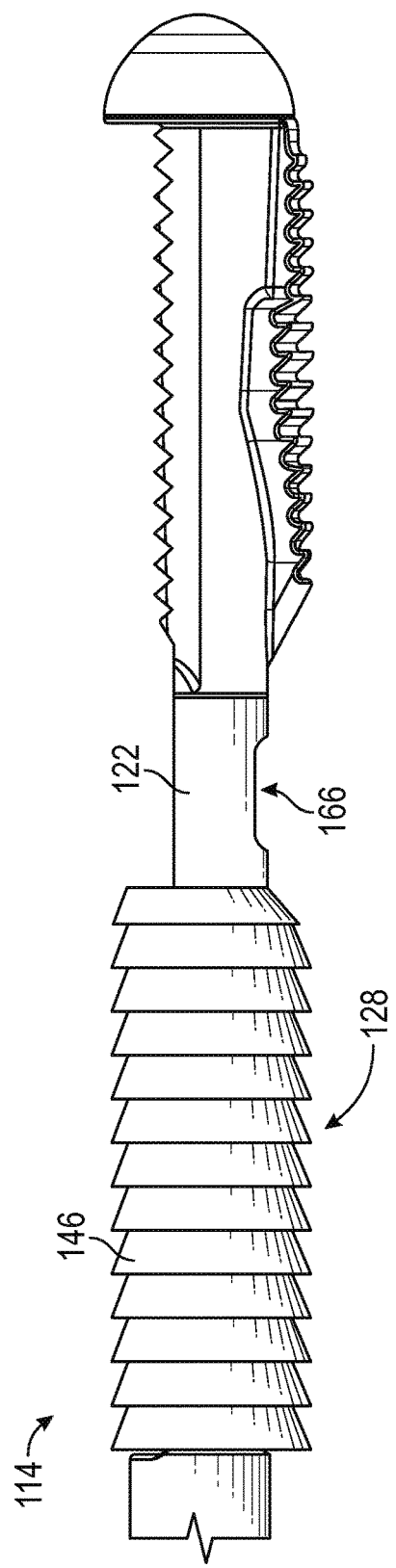
FIG. 12A
FIG. 12B

FIXATION DEVICES METHODS AND SYSTEMS FOR SOFT TISSUE REPAIR

CLAIM OF PRIORITY

This application claims the benefit of U.S. Provisional Patent Application Ser. No. 62/250,719, filed on Nov. 4, 2015, the benefit of priority of which is claimed hereby, and which is incorporated by reference herein in its entirety.

FIELD

The present subject matter relates to surgical procedures and devices and, more particularly, to prostheses, systems and methods related to soft tissue repair.

BACKGROUND

The successful reattachment of soft tissue to bone can be a significant concern, especially in the sports medicine industry.

The majority of soft tissue repairs involve suture anchors or tacks. In such methods, an anchor or tack is readied for insertion into bone and a suture is passed through tissue and the anchor or tack and knotted or otherwise connected thereto. While holding tension on the suture, joint stability is evaluated and the anchor or tack is deployed into the bone, finalizing the repair.

OVERVIEW

This disclosure pertains generally to systems, methods and devices that facilitate the rapid connection of sutures to tissue fixation implants such as a suture anchor. For example, the systems, methods and devices can facilitate the passage of one or more sutures through the suture anchor and the connection of the one or more sutures to the suture anchor with a minimal change in tension on the one or more sutures from prior to and after deployment of the suture anchor into bone. In some examples, the one or more sutures can be cut during deployment of the suture anchor into bone. Deployment of the suture anchor into bone can be accomplished with rapid fixation technology (RFT), which provides the ability to rapidly and precisely deliver the suture anchor to a desired location.

The present inventor has recognized, among other things, that existing soft tissue fixation solutions can require a multiple step process where connection of the suture to the anchor can be challenging. This process can include deploying an anchor into bone and connecting suture(s) to the deployed anchor. It can often be difficult to accomplish such connection as the suture(s) must be knotted or otherwise connected while maintaining the suture at a desired amount of tension. Failure to provide adequate tension (providing too much or too little) can cause the suture(s) to he ineffective necessitating repetition of the entire process in some cases.

Considering these factors, the present inventor proposes an anchoring device and related systems and methods that can reduce the number of currently used surgical processes to provide for faster, easier, and more reproducible surgical techniques. Thus, the present application discloses an anchor device configuration where once a desired degree of tension is provided to the suture, upon deployment of the anchor device, connection of the suture(s) to the anchor is accomplished and the desired tension is substantially maintained during this process. In some examples, the suture(s) can additionally be cut during deployment of the suture(s) anchor into bone, thereby reducing the number of additional steps required during the surgical process.

To further illustrate the apparatuses, systems and methods disclosed herein, the following non-limiting examples are provided:

In Example 1, a device for anchoring sutured tissue to a bone is disclosed. The device can include a body having a wall with an outer surface thereof that can be configured to engage the bone of a patient. The body can define an inner passage extending generally from a proximal end thereof to a distal end thereof and can have a slit formed by the wall thereof. The slit can extend at least a portion of a proximal-distal length of the wall. The device can additionally include a member configured to be disposed within the body and moveable along the inner passage relative to the body between a first position and a second position, wherein the member can be configured with a second passage to receive and pass a suture through the member when the member is in the first position.

In Example 2, the device of Example 1, wherein the member can comprise a bullet having a distal end configured to engage the bone of a patient, the bullet can be configured to remain within the body, and a deployment pin that can be configured to be detachable from the bullet and removable from the body, wherein the deployment pin can be actuateable relative to the body to move the bullet to the second position relative to the body and thereby form a deployed configuration of the device.

In Example 3, the device of Example 2, wherein the deployment pin can form the second passage, and wherein the bullet can be configured to be clear of the first aperture, the second aperture, and the second passage when the member is in the first position.

In Example 4, the device of any one or any combination of Examples 1 to 3, wherein the body can comprise an expandable shell and can have a first aperture and a second aperture formed by the wall thereof. The first and second apertures can be disposed between the proximal end and the distal end, the first aperture can be spaced circumferentially about the wall from the second aperture, the slit can communicate with the second aperture.

In Example 5, the device of Example 4, wherein the member can be configured to be received in the body and can obstruct communication of the first aperture with the second aperture when the member is in the second position.

In Example 6, the device of Example 5, wherein the first and second apertures can comprise outer orifices in communication with the second passage when the member is in the first position, the first and second apertures can be circumferentially opposing one another and generally interfacing through the first passage so as to be co-aligned with one another.

In Example 7, the device of any one or any combination of Examples 1 to 6, wherein the slit can be configured to receive a suture initially inserted through the second aperture, and wherein the slit can facilitate movement of the suture toward the proximal end of the body as the member is moved toward the second position.

In Example 8, the device of any one or any combination of Examples 1 to 7, wherein the member can have a protrusion from an outer surface thereof, the protrusion can be configured to facilitate expansion of the body when the member is in the second position.

In Example 9, the device of Example 8, wherein the protrusion can include a keel configured to form a shearing interface with a portion of a deployment device when the member is in the second position.

In Example 10, the device of Example 8, wherein the protrusion can generally align with the proximal-distal extending slit when the member is in the first position and can include a textured bone engaging surface that is disposed in the slit when the member is in the second position.

In Example 11, the device of any one or any combination of Examples 1 to 10, wherein the member can have a distal end and a proximal end, and wherein the member can be configured to taper from the distal end to the proximal end such that the member has a reduced diameter at the proximal end relative to the distal end.

In Example 12, the device of any one or any combination of Examples 1 to 11, wherein the member can be configured to cause the body to expand when the member is in the second position relative to the first position, and wherein at least one of the member and body can be non-symmetrically arranged with respect to a central axis of a deployment device such that movement of the member toward the second position causes one or more sutures to be cut by a shearing interface between a portion of the member and a distal portion of the cannula.

In Example 13, the device of Example 11, wherein the portion of the member that contacts the deployment device can be configured as a keel and the distal portion of the cannula can be configured as a cutting surface for cutting a suture disposed on the keel.

In Example 14, the device of any one or any combination of Examples 1-13, wherein the member can have a textured portion co-oriented with the first aperture, the textured portion can be configured to engage a suture and generally maintain a position of the suture relative to the member as the member moves from the first position to the second position relative to the body.

In Example 15, the device of Example 14, wherein the textured portion can be recessed relative to a remainder of an outer surface of the member and the recess facilitates passage of the suture between the member and the body as the member moves from the first position to the second position relative to the body.

In Example 16, the device of Example 15, wherein the remainder of the outer surface of the member can have a generally rounded shape and the textured portion can be substantially flat.

In Example 17, a system for anchoring a sutured tissue to a bone is disclosed. The system can comprise one or more sutures, an outer body, an inner bullet, and a surgical tool. The outer body can have a wall with an outer surface configured to engage the bone of a patient. The body can have an inner passage extending generally from a proximal end thereof to a distal end thereof. The body can have a slit formed by the wall thereof, the slit can extend at least a portion of a proximal-distal length of the wall. The inner bullet can be configured to be disposed within the body and can be moveable along the inner passage relative to the body between a first position and a second position, wherein with movement of the bullet toward the second position, the one or more sutures can move proximally from at least one of the first and second apertures toward the proximal end of the body. The surgical tool can be configured to actuate movement of the bullet relative to the body between the first position and the second position.

In Example 18, the system of Example 17, wherein the surgical tool can have an outer cannula, an inner shaft residing inside and movable relative to the outer cannula, and a pin coupled to and extending from a distal end of the inner shaft, and wherein the pin can be configured to couple with the bullet through the body of the anchor.

In Example 19, the system of Example 18, wherein the pin can be configured to be detachable from the bullet and removable from the body, and wherein the pin can form a second passage facilitating communication of the one or more sutures therethrough.

In Example 20, the system of Example 19, can further comprise a threading tool, the threading tool can have a loop configured to receive the one or more sutures and fit through the second passage of the pin.

In Example 21, the system of any one or any combination of Examples 17 to 20, wherein at least one of the outer body and the inner bullet can be non-symmetrically arranged with respect to a central axis of the surgical tool such that movement of the bullet toward the second position can cause the one or more sutures to be cut by a shearing interface between a portion of the bullet and a distal portion of the cannula.

In Example 22, the system of any one or any combination of Examples 17 to 21, wherein the body can have a first aperture and a second aperture formed by the outer wall and circumferentially spaced from one another, the first and second apertures and body can be configured to receive the one or more sutures, and wherein the first and second apertures can allow for passage of the one or more sutures through the body in a direction generally transverse to a direction of movement of the bullet between the first position and the second position.

In Example 23, a two-piece suture anchor for anchoring sutured tissue to a bone is disclosed. The suture anchor can comprise an expandable body and a member. The expandable body can have an inner passage extending generally from a proximal end thereof to a distal end thereof. The body can define a slit communicating with the inner passage. The slit can extend at least a portion of a proximal-distal length of the body. The member can be configured to be disposed within the body and can be moveable along the inner passage relative to the body between a first position and a second position, wherein the member can be configured to cause the body to expand when the member is in the second position relative to the first position. The slit can be configured to receive a suture initially inserted through the member, and wherein the slit can facilitate movement of the suture toward the proximal end of the body as the member is moved toward the second position.

in Example 24, the suture anchor of Example 23, wherein at least one of the member and body can he non-symmetrically arranged with respect to a central axis of a deployment device such that movement of the member toward the second position can cause one or more sutures to be cut by an interference between a portion of the member and a distal portion of the cannula.

in Example 25, the suture anchor of any one or any combination of Examples 23 to 24, wherein the member can have a protrusion from an outer surface thereof, the protrusion can be configured to facilitate expansion of the body when the member is in the second position.

In Example 26, the suture anchor of Example 25, wherein the protrusion can include a keel configured to contact a portion of a deployment device when the member is in the second position.

In Example 27, the suture anchor of Example 25, wherein the protrusion can generally align with a proximal-distal extending slit formed by the wall when the member is in the first position and can include a textured surface that is disposed in the slit when the member is in the second position.

In Example 28, the suture anchor of any one or any combination of Examples 23 to 27, wherein the body can have a first aperture and a generally circumferentially opposing second aperture, and wherein the slit can be configured to communicate with the second aperture to receive the suture which was initially passed through the second aperture.

In Example 29, the suture anchor of any one or any combination of Examples 23 to 28, wherein the slit may not initially extend an entire proximal-distal length of the body, the body can be configured to be split by the member when the member moves from the first position to the second position to further extend the slit the entire proximal distal length of the body.

In Example 30, the apparatuses and systems of any one or any combination of Examples 1-29 can optionally be configured such that all elements or options recited are available to use or select from.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses, systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIGS. 2A to 2C provide plan views from various perspectives of the anchoring device of FIGS. 1A and 1B in a non-deployed position in accordance with an example of the present application.

FIGS. 3A and 3B are cross-sections showing an offset in position between an outer cannula of a deployment device and components of the anchoring device in accordance with an example of the present application.

FIGS. 12A, 12B, and 12C provide plan views from various perspectives of another example of the anchoring device in accordance with an example of the present application.

DETAILED DESCRIPTION

The present application relates to systems, methods and devices that facilitate the rapid connection of sutures to tissue fixation implants such as a suture anchor. For example, the systems, methods and devices can facilitate the passage of one or more sutures through the suture anchor and the connection of the one or more sutures to the suture anchor with a minimal change in tension on the one or more sutures from prior to and after deployment of the suture anchor into bone. In some examples, the one or more sutures can be cut during deployment of the suture anchor into bone. The present systems, methods and devices can be used in conjunction with one or more bone fixation tool (also referred to a "deployment devices" "deployment tool" or simply as a "surgical tool" herein) such as the one as disclosed in U.S. Pat. No. 8,221,433, which is incorporated by reference in its entirety. The methods and devices described herein can use a modified tool similar to that disclosed in the '433 patent. The present tissue fixation implants have applicability to a variety of orthopedic procedures as well as to the sports medicine industry. Thus, the present implants are applicable to the repair of and/or fixation to various anatomical locations and features including, for example, the labrum of the shoulders and hips.

Figure 1A:
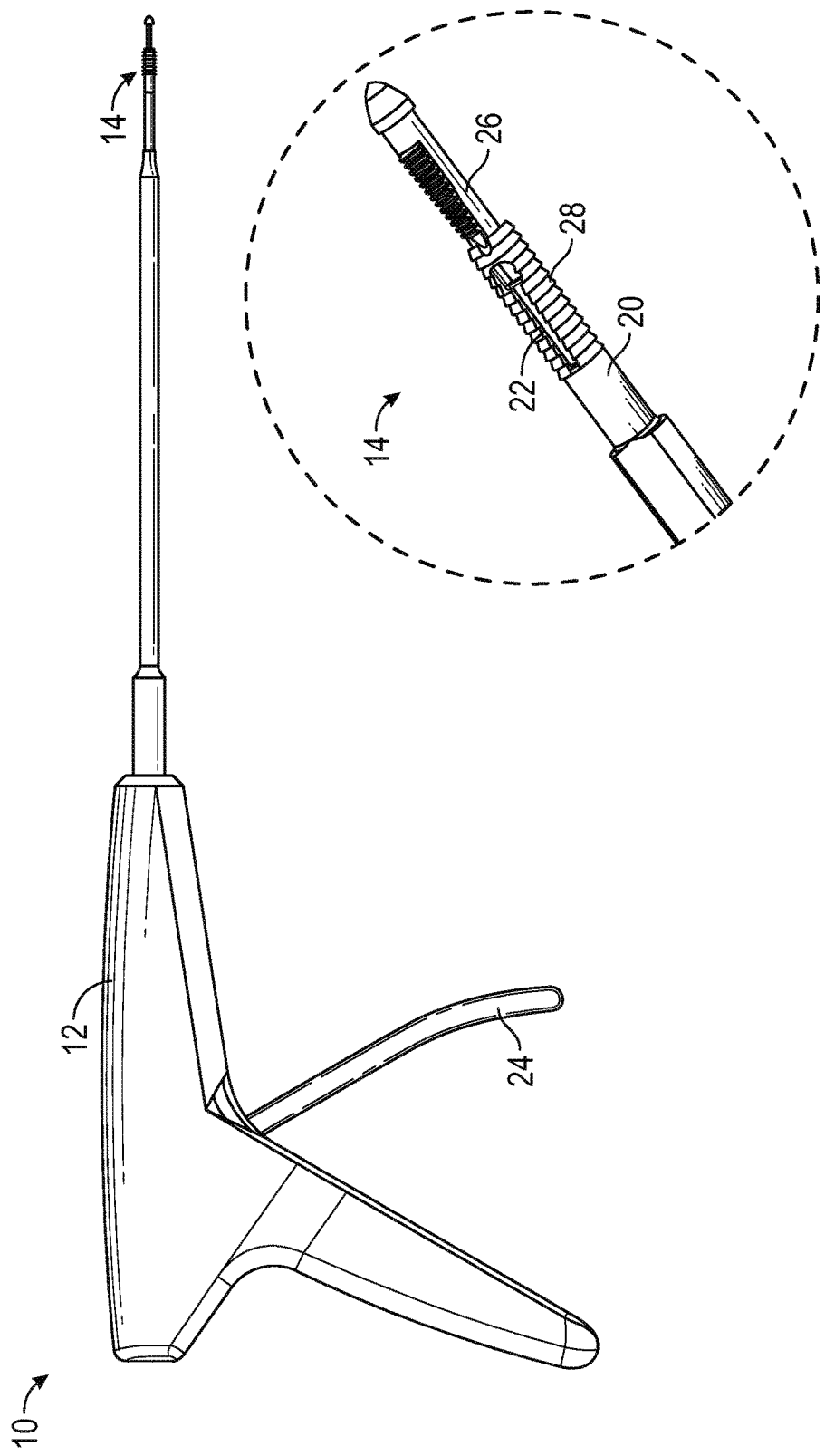
FIGS. 1A and 1B illustrates a system for soft tissue repair in accordance with an example of the present application.
Figure 1B:
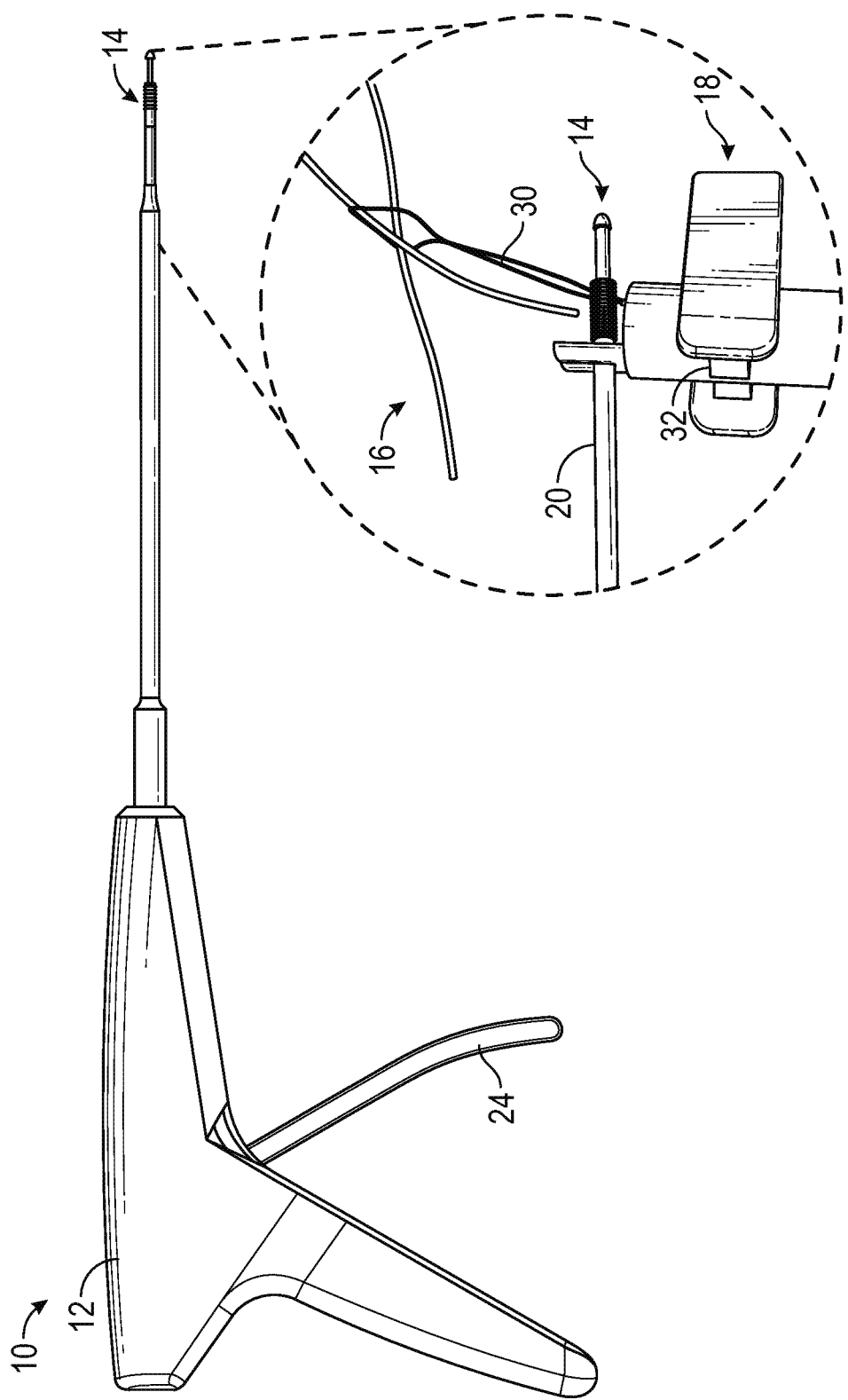

FIGS. 1A and 1B show a system 10 for repair of soft tissue. The system 10 includes a deployment tool 12, an implant 14, one or more sutures 16 (FIG. 1B) and a threading tool 18 (FIG. 1B).

The deployment tool 12 can be configured for facilitating fixation of the implant 14 into bone of a patient. As such, the deployment tool 12 can comprise a tool similar to that disclosed in the '433 patent. As is shown in the enlargement of the distal portion of the deployment tool 12 in FIG. 1A, the deployment tool 12 can have an outer cannula 20, an inner shaft (not shown) residing inside and movable relative to the outer cannula 20, and a pin 22 coupled to and extending from a distal end of the inner shaft. Movement of the inner shaft relative to the outer cannula 20 can be facilitated by a trigger 24. The pin 22 can be configured to couple with the implant 14 and actuate one portion (an inner bullet 26) of the implant 14 relative to another portion (an outer body 28) in a manner to be discussed subsequently. The enlarged view of the distal portion of the deployment tool 12 in FIG. 1A provides examples of the inner bullet 26, the pin 22 and the outer body 28 in a non-deployed first position.

FIG. 1B shows the one or more sutures 16 and the threading tool 18 in further detail. The suture(s) 16 can comprise any type currently known, and thus, can be constructed of various materials and can be monofilament and/or multifilament as desired, for example. The threading tool 18 can include a body portion 30 configured to couple to the outer cannula 20 or another portion of the deployment device 12. The threading tool 18 can additionally include a loop 32 constructed of a flexible material such as fiber. The loop 32 can couple to the body portion 30. The loop 32 is configured for insertion through the outer body 28 of the implant 14 and the pin 22 of the deployment tool 12. More particularly, the loop 32 can be configured to receive the one or more sutures 16 and can fit through first and second apertures of the outer body 28 and a second passage of the pin 22. As will be illustrated and discussed subsequently, the loop 32 can act to draw the suture(s) 16 through the outer body 28 and the pin 22 prior to deployment of the implant 14 into bone. Once the suture(s) 16 has been drawn through the outer body 28 and the pin 22, the threading tool 18 can be removed from the deployment tool 12.

Figure 2A:
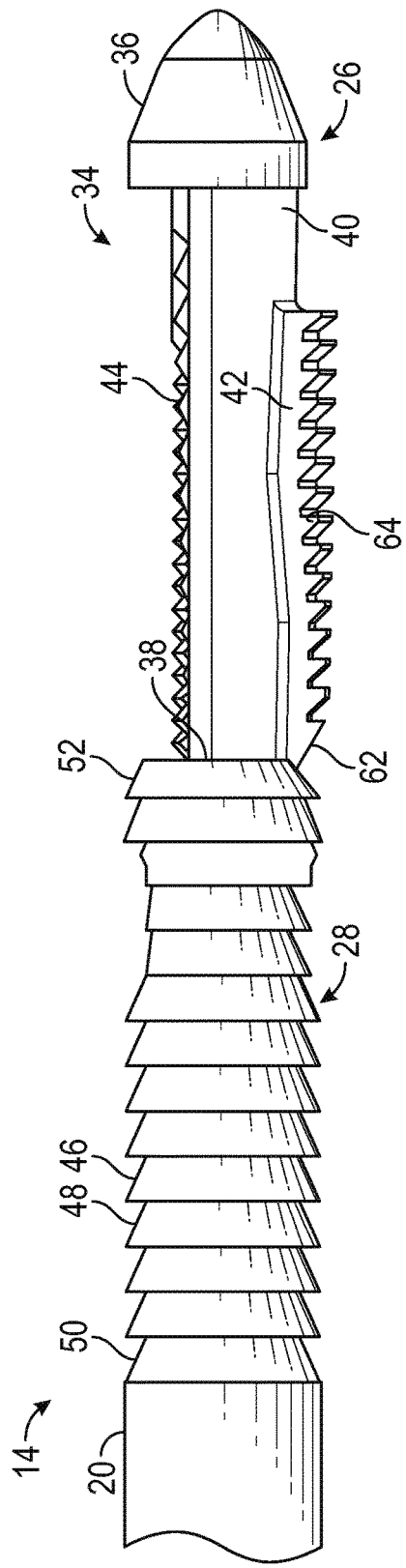
Figure 2B:
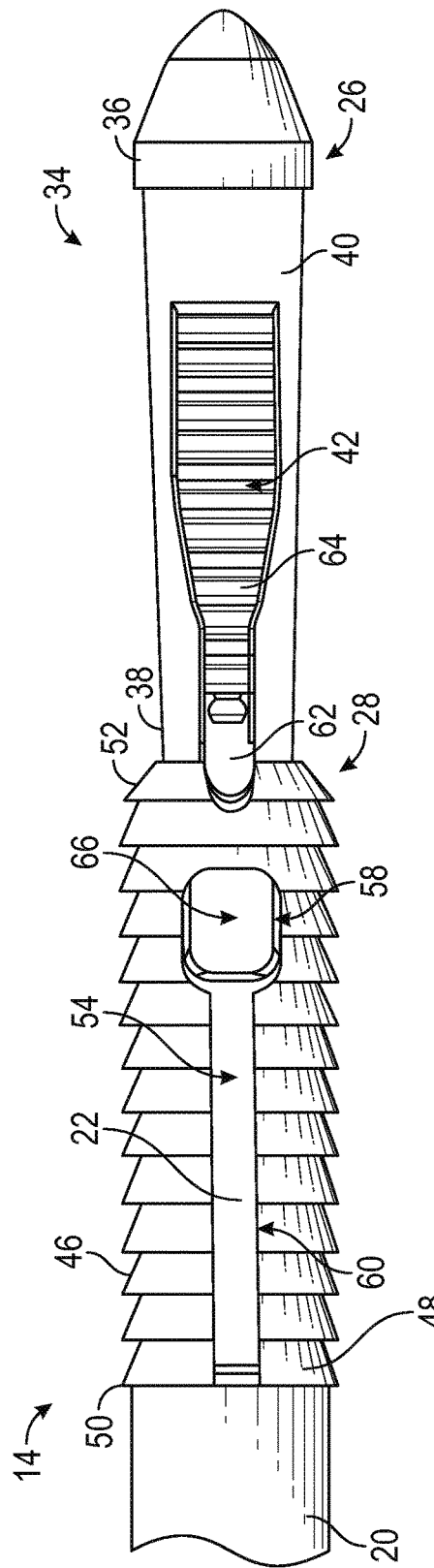

FIGS. 2A to 2C show plan views of the implant 14 and the pin 22 from various perspectives. As discussed previously, the implant 14 can be comprised of the inner bullet 26 and outer body 28. Collectively the inner bullet 26 and the pin 22 can comprise an inner member 34 that is configured to be received in and is moveable relative to the outer body 28 in the manner discussed subsequently, According to the example of FIGS. 2A to 2C, the inner bullet 26 can include a distal end portion 36, a proximal end portion 38, a body 40, a protrusion 42, and a textured portion 44. The outer body 28 can include a wall 46 having a textured outer surface 48, a proximal end portion 50, a distal end portion 52, an inner passage 54 (FIG. 2B see also FIGS. 3A and 3B), a first aperture 56 (FIG. 2C), a second aperture 58 (FIG. 2B), and a slit 60 (FIG. 2B).

As is generally shown in FIGS. 2A to 2C the inner bullet 26 is disposed in a first (non-deployed) position relative to the outer body 28. The inner bullet 26 and the outer body 28 can be configured to couple together in a manner that allows the inner bullet 26 to translate proximally relative to outer body 28 into a second (deployed) position where the inner bullet 26 is received within the outer body 28. More particularly, the pin 22 can be actuateable relative to the outer body 28 to move the inner bullet 26 to the second position relative to the outer body 28 and thereby form a deployed configuration of the implant 14. The pin 22 can be configured to be detachable from the inner bullet 26 and removable from the outer body 28 according to some examples.

The distal end portion 36 of the bullet 26 can be configured as a pointed tip that is configured to engage with bone of the patient. The bullet 26 can taper from the distal end portion 36 to the opposing proximal end portion 38 (i.e. body 36 can generally taper) such that the bullet 26 has a reduced diameter at the proximal end portion 38 relative to the distal end portion 36.

The body 40 can connect the distal end portion 36 to the proximal end portion 38. The protrusion 42 can extend outward from an outer surface of the body 40, and thus, can increase the radial extent thereof. According to some examples the protrusion 42 can include a keel 62 and a textured surface 64 along an outer extent thereof as shown in FIG. 2A. The textured portion 44 can be arranged on a generally opposing circumferential portion of the body 40 from the protrusion 42.

The protrusion 42 can generally align with the proximal-distal extending slit 60 formed by the wall 46 when the member 34 is in the first position. The textured surface 64 thereof can be disposed in the slit 60 when the member 34 is in the second position. As shown in FIGS. 2A and 2C, the remainder of the outer surface of the member 34 (excluding the textured portion 44) can have a generally rounded shape while the textured portion 44 can be substantially flat. The textured portion 44 can he configured to engage a suture (e.g., one or more sutures 16) and generally maintain a position of the suture relative to the member 34 as the member 34 moves from the first position to the second position relative to the outer body 28. According to the illustrated example, the textured portion 44 can be recessed relative to a remainder of an outer surface (e.g. outer surface of body 40) of the member 34 and the recess can facilitate passage of a suture between the member 34 and the outer body 28 as the member 34 moves from the first position to the second position relative to the outer body 28.

Turning to the outer body 28, the wall 46 can separate the generally opposing inner surface from the outer surface 48. The outer surface 48 can be textured or otherwise configured to engage the bone of a patient in some examples. The wall 46 can extend from the proximal end portion 50 to the distal end portion 52 and can define the inner passage 54. In some cases, the wall 46 may not extend entirely circumferentially extend around the inner passage 54 but can be split along the slit 60 (FIG. 2B). The wall 46 can also define the first aperture 56 and the second aperture 58. The first and second apertures 56, 58 can be generally circumferentially opposed and can be generally interfacing with one another so as to be co-aligned. According to some examples the first and second apertures 56, 58 can communicate with the inner passage 54. Additionally, the first and second apertures 56, 58 can be positioned between the proximal end portion 50 to the distal end portion 52. The slit 60 can extend at least a portion of a proximal-distal length of the wall 46 and can communicate with the second aperture 58. The extent of slit 60 can initially be less than an entire proximal-distal length of the wall 46 (i.e. a distal portion of the wall 46 may entirely surround the inner passage 54. However, in some cases slit 60 can be configured to grow to the entire proximal-distal length of the wall 46 upon deployment of the bullet 26. Thus, deployment of the bullet 26 can tear the wall 46 and increase the size of the slit 60. Features such as the keel 62 can facilitate tearing of the wall 46 to further extend the slit 60.

The inner passage 54 can extend generally from the proximal end portion 50 to the distal end portion 52. The pin 22 (and inner member 34) can be configured to facilitate communication of the first aperture 56 with the second aperture 58 via a second passage 66 when the member 34 (the pin 22 and the bullet 26) is in the first position shown in FIGS. 2A to 2C. However, the bullet 26 can be configured to obstruct communication of the first aperture 56 with the second aperture 58 when the bullet 26 is in the second (deployed) position in some examples. In particular, the pin 22 can form the second passage 66 and the bullet 26 can be configured to be clear of (i.e. be distally spaced from) the first aperture 56 and the second aperture 58 when the member 34 is in the first position.

According to some examples, the outer body 28 can comprise an expandable shell constructed of polymeric or other material. In some cases the materials can be resorbable as desired. The expansion of the outer body 28 can be facilitated by the slit 60 along with other structures of the bullet 26 (e.g., the protrusion 42 and the tapered body 40). Thus, the member 34 can be configured to cause the outer body 28 to expand when the member 34 is in the second position (see e.g., FIG. 10) relative to the first position of FIGS. 2A to 2C.

FIGS. 3A and 3B show a cross-section of the outer cannula 20, the outer body 28, and the member 34 including the pin 22 and bullet 26. The cross-section is taken generally along the center of the slit 60 (FIG. 2B) and thus shows half of the protrusion 42 and the textured portion 44. FIGS. 3A and 3B further illustrate the first passage 54, the first aperture 56, and the second aperture 58.

As shown in FIG. 3A, the outer cannula 20 can have a central axis OCA (an axis of symmetry). Similarly, the member 34 (i.e. the pin 22 and bullet 26) and the outer body 28 can have a central axis MBCA. As shown in the example of FIG. 3A, the axis OCA may not align with the axis MBCA. Therefore, the member 34 and outer body 28 can be non-symmetrically arranged with respect to the central axis (the axis OCA) of the deployment device 12 such that movement of the member 34 toward the second position causes one or more sutures to be cut by interaction (e.g. interference) between a portion of the member 34 and a distal portion of the outer cannula 20.

FIG. 3B illustrates movement of member 34 (the pin 22 and the bullet 26) relative to the outer body 28 with arrow A. Arrows $A_1$ and $A_2$ further illustrate expansion of the outer body 28 due to movement of the member 34 toward the second position (shown in FIG. 10). Expansion of the member 34 and/or the non-symmetry of the member 34 can bring the keel 62 into contact with a portion (e.g., the outer cannula 20) of the deployment tool 12 (FIGS. 1A and 1B) when the member 34 is in the second position. Thus, the keel 62 can be angled or otherwise configured to contact a portion of the deployment tool 12 when the member 34 is in the second position. According to some examples, the distal portion of the outer cannula 20 can be configured as a cutting surface 70 for cutting suture disposed on the keel 62.

The first and second apertures 56, 58 can allow for passage of one or more sutures (see e.g., FIGS. 1B and 4-12B) through the outer body 28 in a direction generally transverse to a direction of movement (as indicated by arrow A) of the bullet 26 between the first position and the second position.

Thus, according to some examples the anchor can include an outer expandable body and an inner tapered body. A deployment shaft (e.g. pin 22) can pass through the expandable body and attach to the distal tapered body. Suture(s) can be passed through the expandable outer body and the deployment shaft. The outer cannula can be configured to hold the outer body in proximal-distal position beneath the bone surface while the deployment shaft is actuated to deploy the anchor. Actuating the deployment shaft to translate the tapered body proximally into the expandable body can cause the outer body to expand into bone. The expansion of the outer body can provide for fixation in the bone. The translation of the inner tapered body against the inner wall of the outer body can prevent the suture(s) from translating with respect to the anchor. The deployment shaft can be released from the tapered inner body and can be removed from the anchor entirely. The suture(s) can be cut during translation of the deployment shaft via a severing action between the inner shaft and the outer cannula according to one example.

Figure 4:
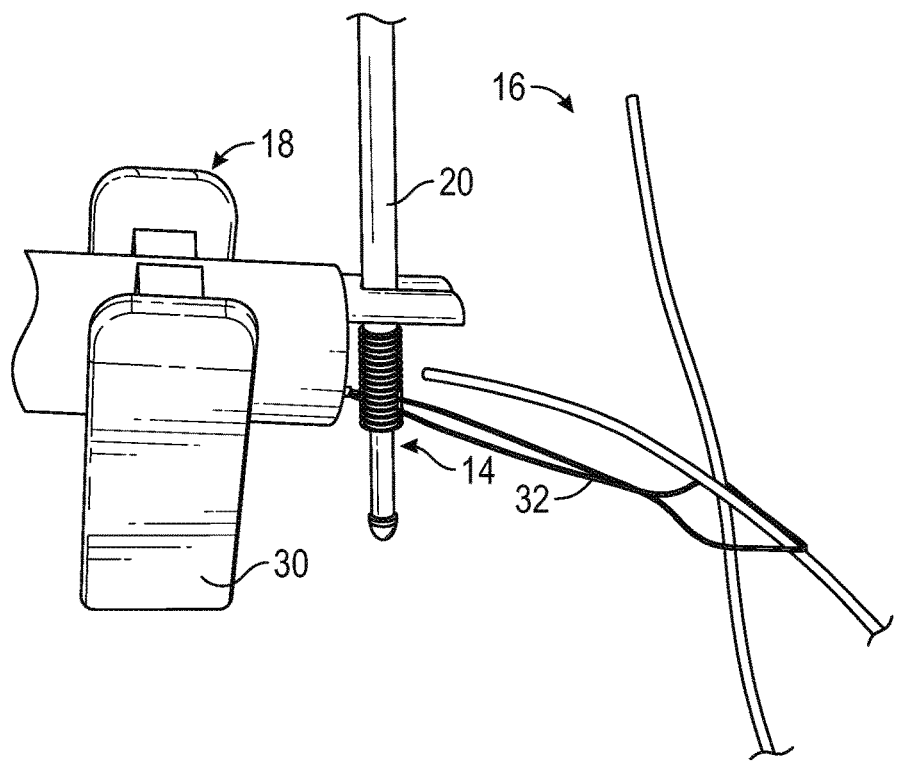
FIGS. 4-11B show a method of deploying the anchoring device for anchoring a sutured tissue to bone in accordance with an example of the present application.
Figure 5:
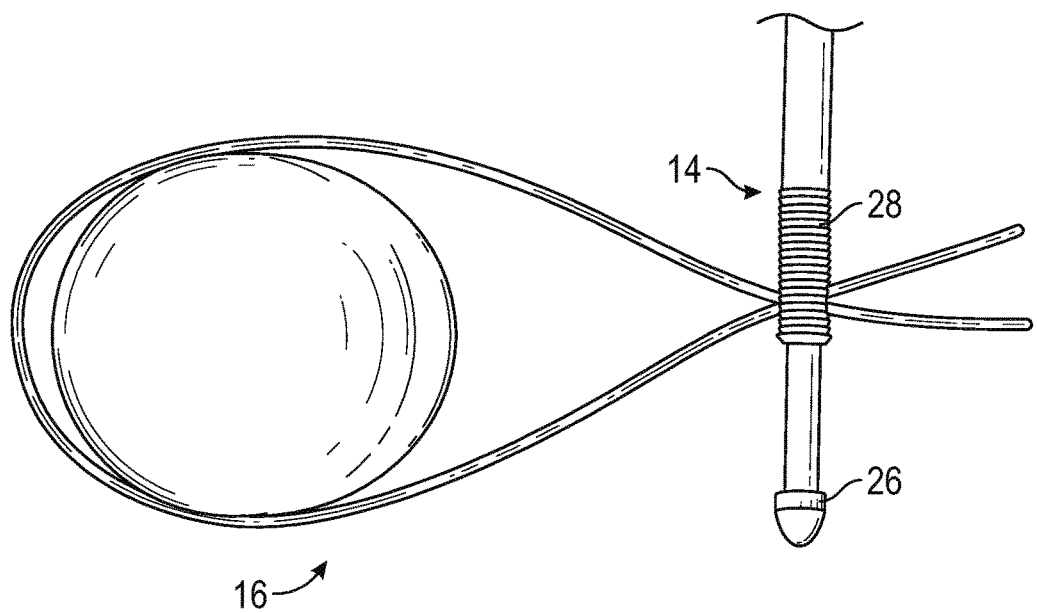
Figure 5A:
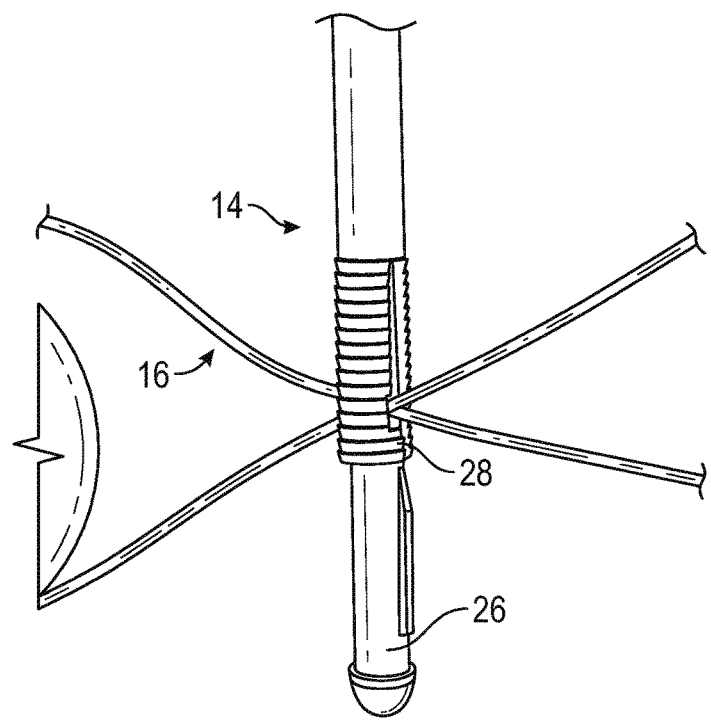

FIGS. 4 to 11B show an exemplary method of deploying an anchoring device such as implant 14 for anchoring a sutured tissue to a bone. FIG. 4 shows the threading tool 18 previously discussed in reference to FIG. 1B being coupled to the outer cannula 20 of the deployment tool 12. As discussed, the loop 32 can be inserted through the implant 14. FIG. 4 also shows the one or more sutures 16 being passed through the loop 32 so as to be captured thereby. This can occur before or after the suture is passed through soft tissue. The implant 14 can be located at a desired bone site such as adjacent the soft tissue as illustrated in FIGS. 5 and 5A. FIGS. 5 and 5A also illustrate that the threading tool 18 can be used to draw the suture(s) 16 through the implant 14 in particular through outer body 28. In doing so, the suture(s) pass through the pin 22 (FIG. 1B) housed within the outer body 28 in the first (non-deployed) position but are clear of the bullet 26 disposed distal thereto.

Figure 6:
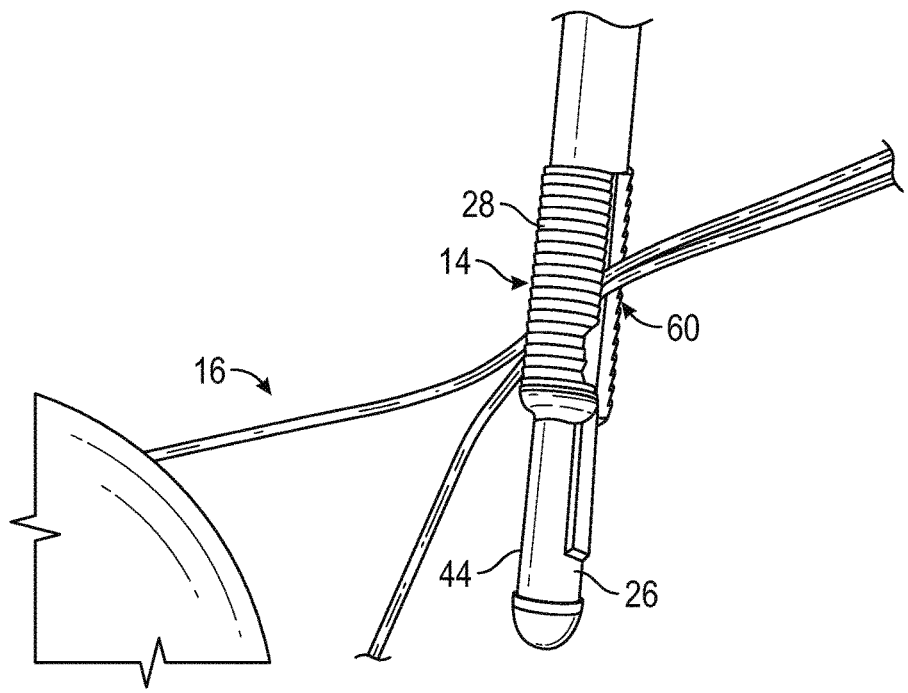

Deployment of the implant 14 is begun in FIG. 6. As shown in FIG. 6, the distal tapered bullet 26 translates proximally up into outer body 28. This action causes the suture(s) 16 to move proximally along slit 60 with the pin 22 (FIGS. 1B and 11) (recall the pin 22 can be coupled to and actuate the bullet 26).

Figure 7:
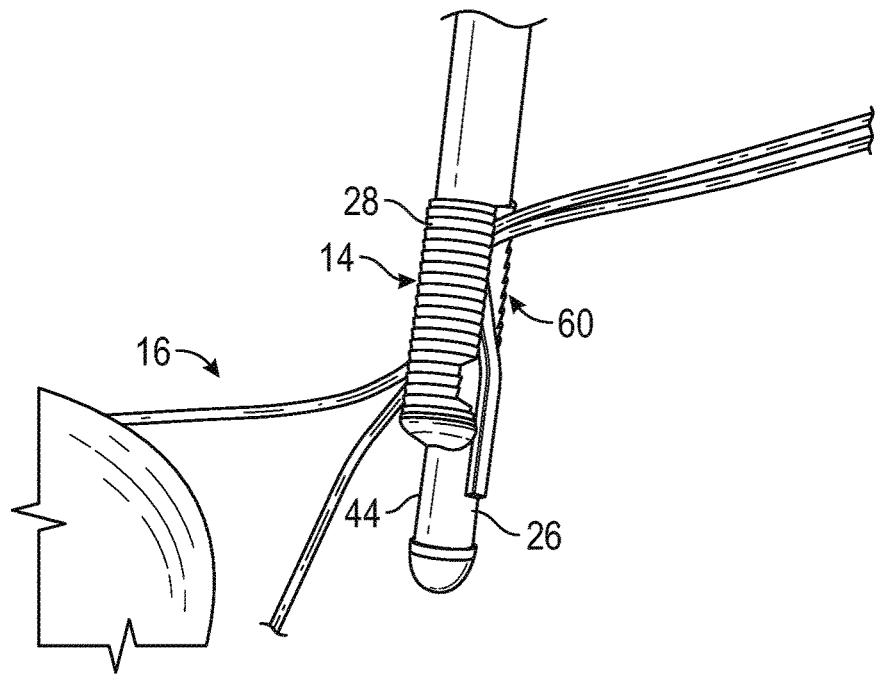
Figure 8:
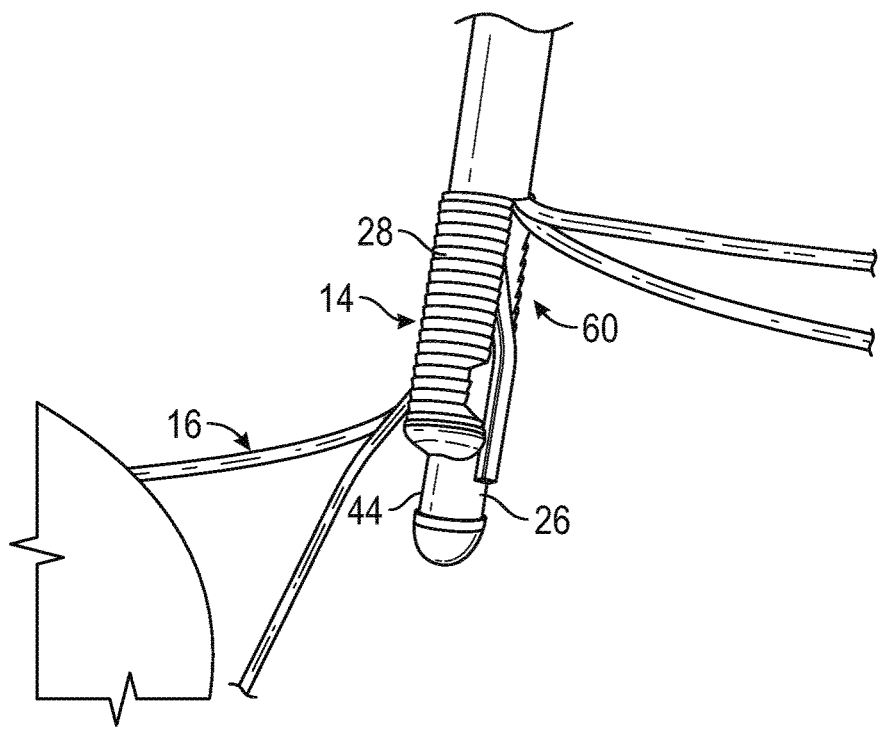

The recessed texture portion 44 of the bullet 26 can grasp and lock the suture(s) 16 between the outer expandable body 28 during the proximal translation. FIGS. 7 and 8 illustrate further proximal translation of the bullet 26 relative to the outer body 28 which can result in movement of the suture(s) 16 proximally up slit 60, diametrical expansion of the outer body 28 and further locking of the suture(s) 16 between the bullet 26 and the outer body 28 on the texture portion 44 side of the implant 14. Thus, the slit 60 can be configured to receive the suture initially inserted through the second aperture 58, and can facilitate movement of the suture toward the proximal end of the outer body 28 as the bullet 26 is moved toward the second position.

Figure 9:
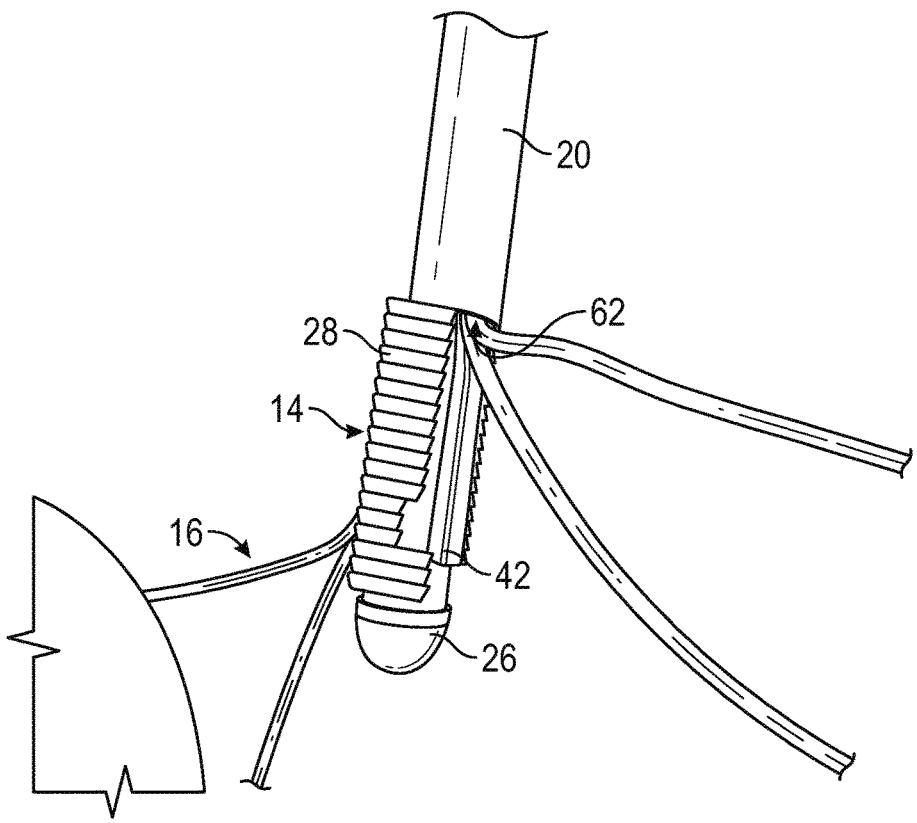

FIG. 9 shows the implant 14 in the second (deployed) position. This position can result in full diametrical expansion of the outer body 28 and disposition of the suture(s) 16 between the lower distal portion (one or more surfaces) of the outer cannula 20 and the keel 62 of protrusion 42. The disposition of the suture(s) 16 between the lower distal portion (one or more surfaces) of the outer cannula 20 and the keel 62 can result in cutting of the suture(s 16 at the proximal end of the implant 14 as illustrated in FIGS. 11A and 11B.

Figure 10:
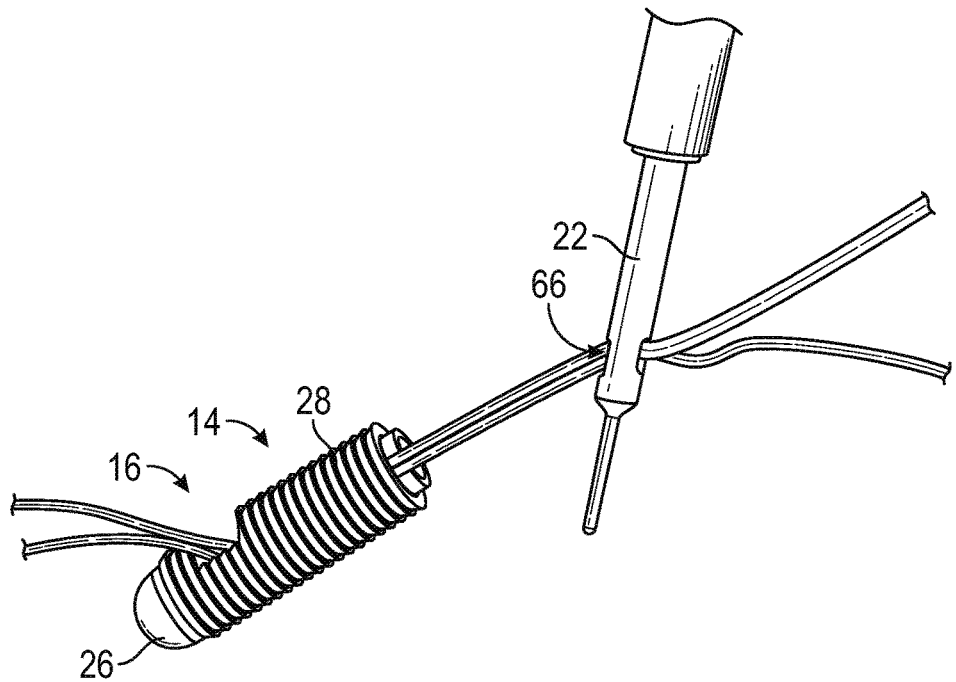

FIG. 10 shows the pin 22 removed from the deployed implant 14 (i.e. the bullet 26 can be fully received in outer body 28 and the suture(s) 16 can pass therebetween). In the example of FIG. 11, the suture(s) 16 are not cut by the deployment of the implant 14 such that the suture(s) 16 remain passing through the second passage 66 formed by the pin 22. This can allow the suture(s) 16 to be drawn a further distance proximally out of implant 14 prior to being cut as desired.

Figure 11A:
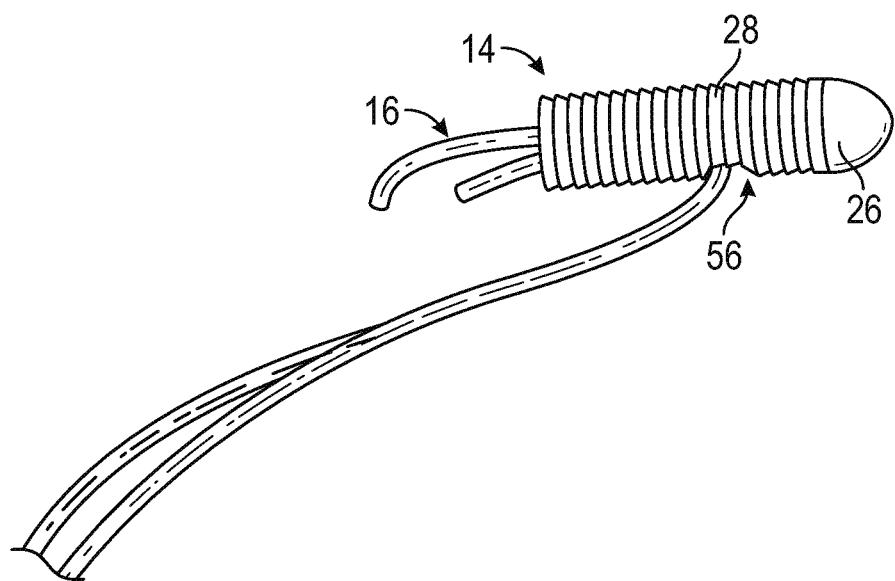
Figure 11B:
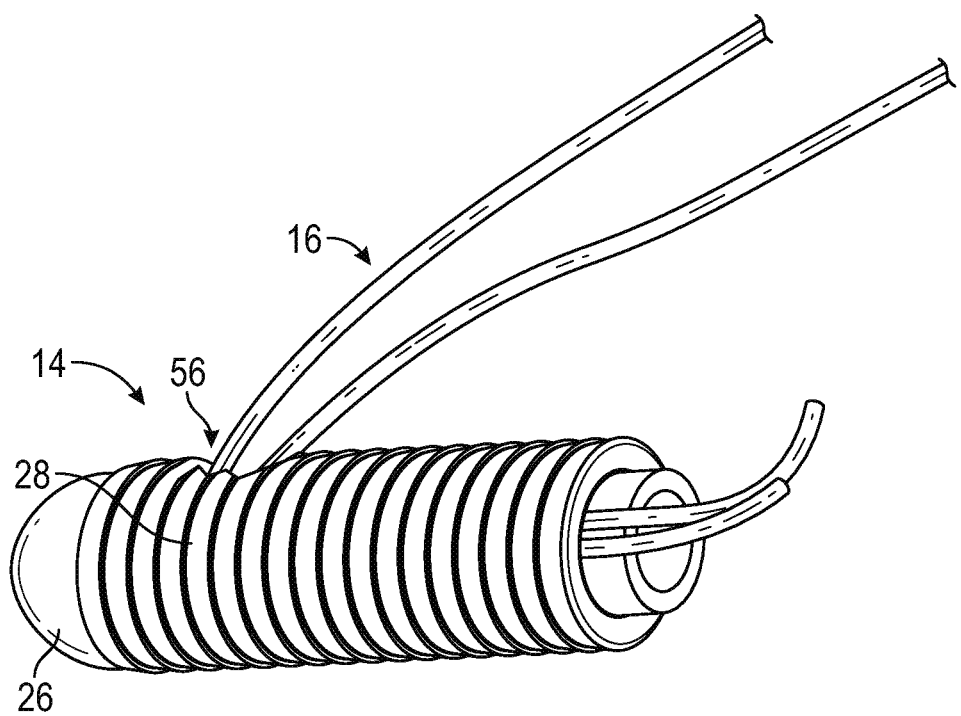

FIGS. 11A and 11B show the implant 14 fully deployed with the suture(s) 16 passing therethrough (e.g., passing through the first aperture 56, captured between the bullet 26 and the outer body 28, and passing out of the proximal end) with the proximal portion of the suture(s) 16 cut. As discussed the suture(s) 16 can be locked within the implant 14 and may be compressed by the force of bone pushing against the wall 46 of the outer body 28.

Figure 12C:
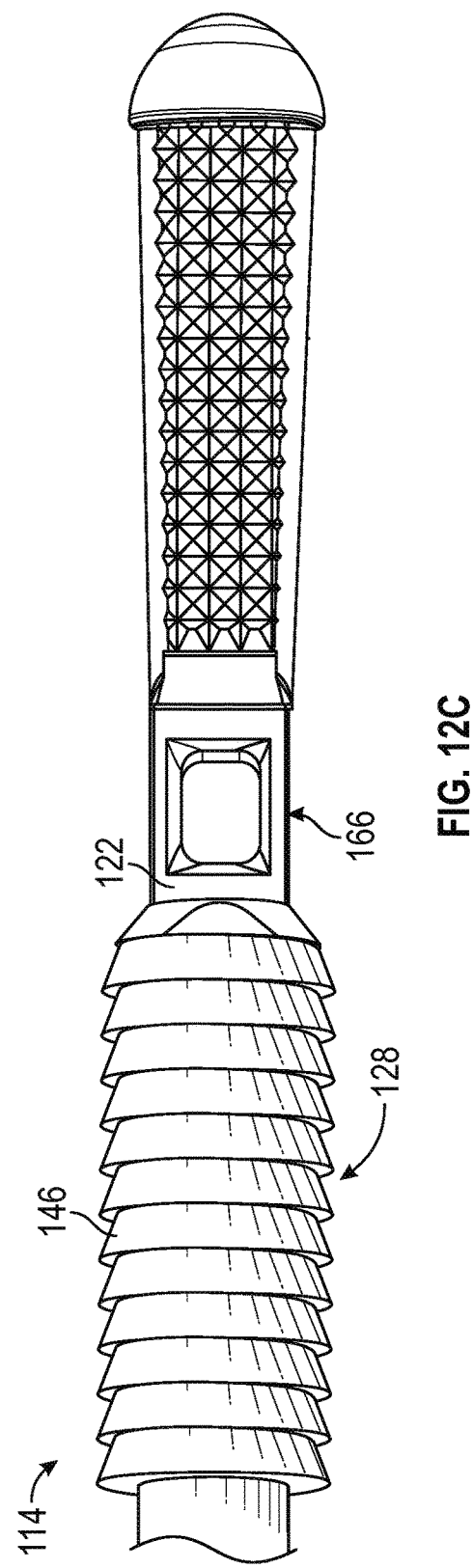

FIGS. 12A, 12B, and 12C show another example of an implant 114. The implant 114 is constructed in a manner similar to that of implant 14 previously discussed, and therefore, a detailed description of the implant 114 will not be provided. The implant 114 differs from implant 14 in that an outer body 128 does not include apertures configured to receive suture. Rather the pin 122 is exposed distal of the outer body 128 and forms a second passage 166 that is subsequently drawn into the outer body 128 with the sutures carried along a slit 160 (FIG. 2A) in a wall 146 as previously described. In other words, the slit 160 does not communicate with an aperture as is the case with implant 14. All other structures and functions of the implant 114 otherwise remain similar to those described previously with respect to implant 14.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

in this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. example, the above-described examples (or one or more aspects thereof) can he used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A device for anchoring sutured tissue to a bone, the device comprising:
   a body having a wall with an outer surface thereof configured to engage the bone of a patient, the body defining an inner passage extending generally from a proximal end thereof to a distal end thereof, the body having a slit formed by the wall thereof, the slit extending at least a portion of a proximal-distal length of the wall; and
   a member configured to be disposed within the body and moveable along the inner passage relative to the body between a first position and a second position, wherein the member is configured with a second passage to receive and pass a suture through the member when the member is in the first position, wherein the member is configured to cause the body to expand when the member is in the second position relative to the first position, and wherein at least one of the member and body are non-symmetrically arranged with respect to a central axis of a deployment device such that movement of the member toward the second position causes one or more sutures to be cut by a shearing interface between a portion of the member and a distal portion of a cannula of the deployment device.

2. The device of claim 1, wherein the member comprises:
   a bullet having a distal end configured to engage the bone of the patient, the bullet configured to remain within the body; and
   a deployment pin configured to be detachable from the bullet and removable from the body, wherein the deployment pin is actuateable relative to the body to move the bullet to the second position relative to the body and thereby form a deployed configuration of the device.

3. The device of claim 2, wherein the deployment pin forms the second passage, wherein the body includes a first aperture and a second aperture formed by the wall thereof, and wherein the bullet is configured to be clear of the first aperture, the second aperture, and the second passage when the member is in the first position.

4. The device of claim 1, wherein the body comprises an expandable shell and has a first aperture and a second aperture formed by the wall thereof, the first and second apertures are disposed between the proximal end and the distal end, the first aperture spaced circumferentially about the wall from the second aperture, the slit communicating with the second aperture.

5. The device of claim 4, wherein the member is configured to be received in the body and to obstruct communication of the first aperture with the second aperture when the member is in the second position.

6. The device of claim 5, wherein the first and second apertures comprise outer orifices in communication with the second passage when the member is in the first position, the first and second apertures circumferentially opposing one another and generally interfacing through the first passage so as to be co-aligned with one another.

7. The device of claim 4, wherein the slit is configured to receive the suture initially inserted through the second aperture, and wherein the slit facilitates movement of the suture toward the proximal end of the body as the member is moved toward the second position.

8. The device of claim 1, wherein the member has a protrusion from an outer surface thereof, the protrusion is configured to facilitate expansion of the body when the member is in the second position.

9. The device of claim 8, wherein the protrusion forms a shearing interface with a portion of the deployment device when the member is in the second position.

10. The device of claim 8, wherein the protrusion generally aligns with the slit when the member is in the first position and includes a textured bone engaging surface that is disposed in the slit when the member is in the second position.

11. The device of claim 1, wherein the member has a distal end and a proximal end, and wherein the member is configured to taper from the distal end to the proximal end of the member such that the member has a reduced diameter at the proximal end of the member relative to the distal end of the member.

12. The device of claim 1, wherein a portion of the member that contacts the deployment device is configured as a protrusion and the distal portion of the cannula is configured as a cutting surface for cutting the suture disposed on the protrusion.

13. The device of claim 1, wherein the body includes a first aperture and a second aperture formed by the wall thereof, wherein the member has a textured portion co-oriented with the first aperture, the textured portion configured to engage the suture and generally maintain a position of the suture relative to the member as the member moves from the first position to the second position relative to the body.

14. The device of claim 13, wherein the textured portion is recessed relative to a remainder of an outer surface of the member and the recess facilitates passage of the suture between the member and the body as the member moves from the first position to the second position relative to the body.

15. The device of claim 14, wherein the remainder of the outer surface of the member has a generally rounded shape and the textured portion is substantially flat.

16. A system for anchoring a sutured tissue to a bone, the system comprising:
one or more sutures;
an outer body having a wall with an outer surface configured to engage the bone of a patient, the outer body having an inner passage extending generally from a proximal end thereof to a distal end thereof, the outer body having a slit formed by the wall thereof, the slit extending at least a portion of a proximal-distal length of the wall, the outer body including a first aperture and a second aperture formed by the wall thereof;
an inner bullet configured to be disposed within the outer body and moveable along the inner passage relative to the body between a first position and a second position, wherein with movement of the inner bullet toward the second position the one or more sutures move proximally from at least one of the first and second apertures toward the proximal end of the outer body; and
a surgical tool having an outer cannula, the surgical tool configured to actuate movement of the inner bullet relative to the outer body between the first position and the second position, wherein at least one of the outer body and the inner bullet are non-symmetrically arranged with respect to a central axis of the surgical tool such that movement of the inner bullet toward the second position causes the one or more sutures to be cut by a shearing interface between a portion of the inner bullet and a distal portion of the outer cannula.

17. The system of claim 16, wherein the surgical tool has an inner shaft residing inside and movable relative to the outer cannula, and a pin coupled to and extending from a distal end of the inner shaft, and wherein the pin is configured to couple with the inner bullet through the outer body.

18. The system of claim 17, wherein the pin is configured to be detachable from the inner bullet and removable from the outer body, and wherein the pin forms a second passage facilitating communication of the one or more sutures therethrough.

19. The system of claim 18, further comprising a threading tool, the threading tool having a loop configured to receive the one or more sutures and fit through the second passage of the pin.

20. The system of claim 16, wherein the outer body comprises a first aperture and a second aperture formed by the wall and circumferentially spaced from one another, the first and second apertures and the outer body configured to receive the one or more sutures, and wherein the first and second apertures avow for passage of the one or more sutures through the outer body in a direction generally transverse to a direction of movement of the inner bullet between the first position and the second position.

21. A two-piece suture anchor for anchoring sutured tissue to a bone, the suture anchor comprising: an expandable body having an inner passage extending generally from a proximal end thereof to a distal end thereof, the expandable body defining a slit communicating with the inner passage, the slit extending at least a portion of a proximal-distal length of the expandable body; and a member configured to be disposed within the expandable body and moveable along the inner passage relative to the expandable body between a first position and a second position, wherein the member is configured to cause the expandable body to expand when the member is in the second position relative to the first position; wherein the slit is configured to receive a suture initially inserted through the member, and wherein the slit facilitates movement of the suture toward the proximal end of the expandable body as the member is moved toward the second position, wherein the slit does not initially extend an entire proximal-distal length of the expandable body, the expandable body is configured to be split by the member when the member moves from the first position to the second position to further extend the slit the entire proximal distal length of the expandable body.

22. The suture anchor of claim 21, wherein at least one of the member and expandable body are non-symmetrically arranged with respect to a central axis of a deployment device such that movement of the member toward the second position causes the suture to be cut by an interference between a portion of the member and a distal portion of a cannula of the deployment device.

23. The suture anchor of claim 21, wherein the member has a protrusion from an outer surface thereof, the protrusion is configured to facilitate expansion of the expandable body when the member is in the second position.

24. The suture anchor of claim 23, wherein the protrusion is configured to contact a portion of a deployment device when the member is in the second position.

25. The suture anchor of claim 23, wherein the protrusion generally aligns with the slit formed by the wall when the member is in the first position and includes a textured surface that is disposed in the slit when the member is in the second position.

26. The suture anchor of claim 21, wherein the expandable body has a first aperture and a generally circumferentially opposing second aperture, and wherein the slit is configured to communicate with the generally circumferentially opposing second aperture to receive the suture which was initially passed through the generally circumferentially opposing second aperture.

* * * * *

UNITED STATES PATENT AND TRADEMARK OFFICE
CERTIFICATE OF CORRECTION

PATENT NO. : 10,548,586 B2  
APPLICATION NO. : 15/338945  
DATED : February 4, 2020  
INVENTOR(S) : Gregory J. Denham Page 1 of 1

It is certified that error appears in the above-identified patent and that said Letters Patent is hereby corrected as shown below:

On the Title Page

On page 2, in Column 1, under "Other Publications", Line 11, delete "Requirmeent" and insert --Requirement-- therefor In the Claims In Column 14, Line 1, in Claim 20, delete "avow" and insert --allow-- therefor In Column 14, Line 6, in Claim 21, after "comprising:", insert --¶--

In Column 14, Line 11, in Claim 21, after "and", insert --¶--

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*